United States Patent [19]

Dasgupta et al.

[11] Patent Number: 5,573,651
[45] Date of Patent: Nov. 12, 1996

[54] APPARATUS AND METHOD FOR FLOW INJECTION ANALYSIS

[75] Inventors: Purnendu K. Dasgupta; Shaorong Liu, both of Lubbock, Tex.

[73] Assignee: The Dow Chemical Company, Midland, Mich.

[21] Appl. No.: 455,581

[22] Filed: May 31, 1995

Related U.S. Application Data

[63] Continuation-in-part of Ser. No. 423,619, Apr. 17, 1995, abandoned.

[51] Int. Cl.[6] .......................... G01N 27/26; G01N 27/447
[52] U.S. Cl. ......................... 204/601; 204/603; 204/604; 204/630; 417/49; 417/50
[58] Field of Search ............................... 204/299 R, 301, 204/601, 603, 604, 630; 417/50, 49

[56] References Cited

U.S. PATENT DOCUMENTS

| | | | |
|---|---|---|---|
| 4,140,121 | 2/1979 | Kühl et al. ............................... | 128/260 |
| 4,908,116 | 3/1990 | Zare et al. ........................... | 204/299 R |
| 4,936,974 | 6/1990 | Rose et al. ........................... | 204/299 R |
| 5,015,350 | 5/1991 | Wiktorowicz ....................... | 204/180.1 |
| 5,021,646 | 6/1991 | Weinberger et al. .............. | 250/227.11 |
| 5,092,972 | 3/1992 | Ghowsi ................................ | 204/182.1 |
| 5,110,424 | 5/1992 | Chin .................................... | 204/108.1 |
| 5,116,471 | 5/1992 | Chien et al. ......................... | 204/180.1 |
| 5,151,164 | 9/1992 | Blanchard et al. ................. | 204/182.1 |
| 5,169,510 | 12/1992 | Lunte et al. ...................... | 204/299 R |
| 5,282,942 | 2/1994 | Herrick et al. ...................... | 204/183.2 |
| 5,358,612 | 10/1994 | Dasgupta et al. .................... | 204/180.1 |
| 5,433,838 | 7/1995 | Dasgupta et al. ................... | 204/299 R |

OTHER PUBLICATIONS

Dasgupta et al., Electroosmosis: A Reliable Fluid Propulsion System for Flow Injection Analysis, Anal. Chem, 66, pp. 1792–1798 Jun. 1994.

Dasgupta et al., Suppressed Conductometric Capillary Electrophoresis, Separation Systems, Am. Chemical Soc., 65, pp. 1003–1011 Apr. 1993.

Jorgenson et al., Zone Electrophoresis in Open–Tubular Glass Capillaries, Anal. Chem, 53, pp. 1298–1302 Jul. 1981.

Liu et al., Electroosmotically pumped capillary flow–injection analysis, Analytica Chimica Acta, 1993, 283, pp. 739–745 (no month provided).

Liu et al., Flow–injection analysis in the capillary format using electroosmotic pumpting, 1992, Analytica Chimica Acta, 268, pp. 1–6 (no month provided).

Wim Th. Kok, Off–Column Detection with Pressure Compensation in Capillary Electrophoresis, Anal. Chem., 65, pp. 1853–1860 Jul. 1993.

Eli Grushka, Effect of hydrostatic flow on the efficiency in capillary electrophoresis, J. of Chromatography, 1991, 559, pp. 81–93 (no month).

(List continued on next page.)

Primary Examiner—Arun S. Phasge
Attorney, Agent, or Firm—Linda Blair Meier

[57] ABSTRACT

Method and apparatus for flow injection analysis (FIA) using an electroosmotic pump. The apparatus includes: an electroosmotic pump having a grounding joint; a sample injection valve for introducing a sample into a carrier stream which valve is in fluid communication with the grounding joint by way of a conduit; a dispersion coil in fluid communication with the sample injection valve; and a detector which is in fluid communication with the dispersion coil. The grounding joint couples the electroosmotic pumping system and the FIA system but electrically isolates them.

Generally, the method utilizes one fluid which is electroosmotically pumped to propel a carrier for flow injection analysis at a controllable flow rate. More specifically, the method includes the steps of: adding a sample to a liquid carrier stream to form a sample zone in the carrier stream; flowing a liquid pumping stream by electroosmosis; and connecting the pumping stream with the carrier stream to propel the carrier stream.

3 Claims, 4 Drawing Sheets

OTHER PUBLICATIONS

Bahowick et al., Sequential Chromatogram Ratio Technique: Evaluation of the Effects of Retention Time Precision, Adsorption Isotherm Linearity, and Detector Linearity on Qualitative and Quantitative Analysis, Anal. Chem. 64, 489–496 Mar. 1992.

van der Schoot et al., Microsystems for Flow Injection Analysis, 1993, Anal. Methods and Instrumentation, vol. 1, No. 1, 38–42 (no month provided).

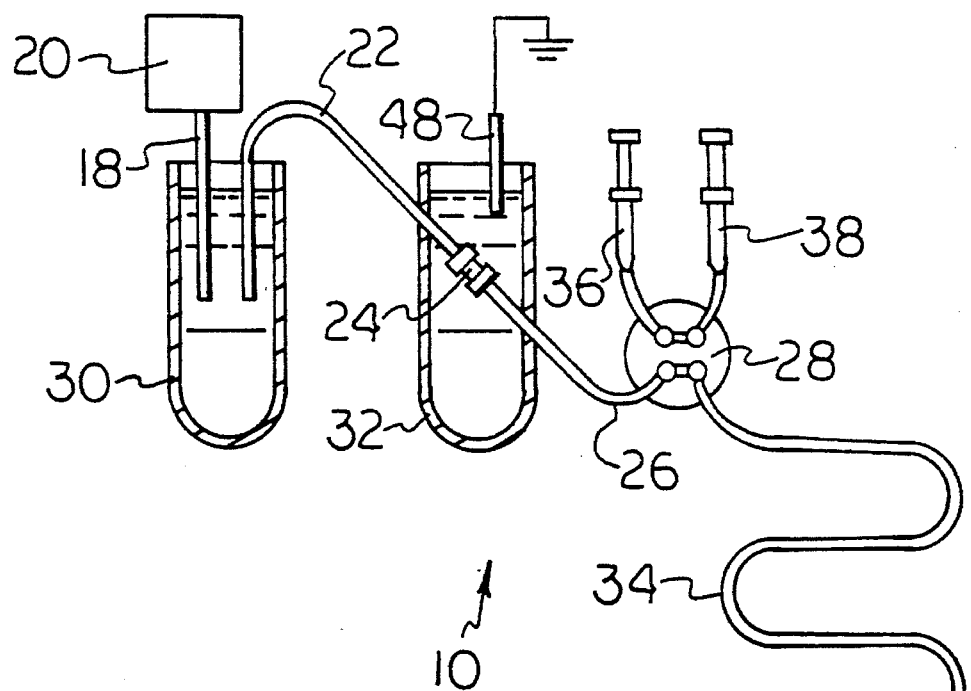
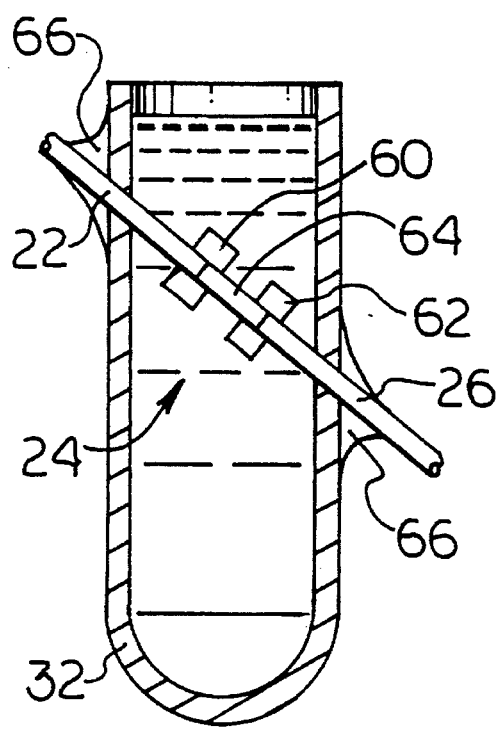
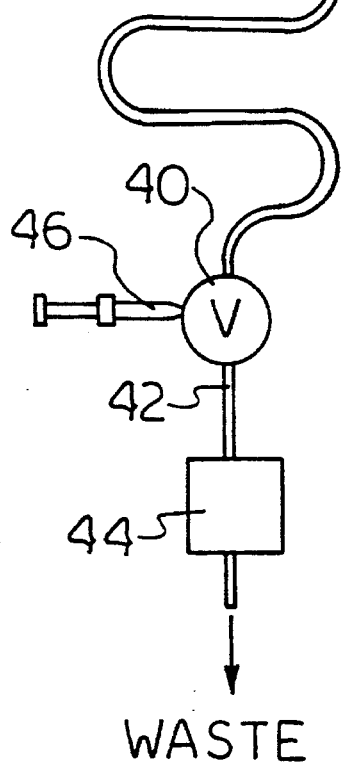
Fig. 1
Fig. 2

APPARATUS AND METHOD FOR FLOW INJECTION ANALYSIS

This application is a continuation in part of patent application Ser. No. 08/423,619, filed Apr. 17, 1995, now abandoned which is herein fully incorporated by reference.

BACKGROUND OF THE INVENTION

Flow injection analysis (FIA) is a well known chemical analysis technique. Miniaturization of an FIA system provides additional benefits to this technique such as a reduction in consumables and generation of waste. However, miniaturization is limited, in part, by the availability of pumping systems of stable flow rates in the sub-microliter per minute domain. Thus, the fluid propulsion device is an important component in a sophisticated FIA system.

Typical fluid propulsion systems for FIA fall into one of two categories: mechanically driven or constant pressure driven. These systems include multiroller peristaltic pumps, piston (syringe type or reciprocating positive displacement type) pumps, gas-pressurized reservoirs or constant-head vessels, and piezoelectric micropumps. Unfortunately, these traditional pumping systems do not provide pumping means as reliable or affordable as desired at low flow rates.

The utilization of electroosmotic flow (EOF) as a fluid propulsion means provides a different category of pumps to the practice of FIA and other flow analysis systems. Other factors remaining the same, the magnitude and the direction of flow in an EOF pump can be readily changed by changing the current, which is linearly proportional to the volumetric flow rate, and by changing the applied voltage, which is linearly proportional to the pressure generated.

Another type of electroosmosis can also be used to generate flow which involves passing a solvated ion from one side of a compartmented chamber to another. Such electrodialysis/electroosmosis based pumps have been patented (U.S. Pat. No. 4,140,121), however, they require carefully chosen electrolytes and electrodes to eliminate gas evolution.

The feasibility of EOF pumped systems in FIA has been demonstrated using capillary electrophoresis (CE) like configurations in which the potential is applied across the entire reaction conduit. See, for example, Liu, S.; Dasgupta, P. K. *Anal. Chim. Acta* 1992, 268, 1–6. Any differences in migration rates between two sequentially introduced zones lead to zone interpenetration that can be carried out in a controlled manner. Any combination of adjacent zones can be mixed in this fashion, unless the species of interest in both such zones are electrically uncharged. Advantages of utilizing an EOF pump in this format include: analyte enrichment by electrostacking, assuming conductance of the sample solution is significantly lower than that of the reagent carrier solution; limited dispersion despite long reaction times and continuous flow; and separation of different reactive constituents of the sample and/or separation of the sample matrix from the constituent of interest.

Despite the advantages of using EOF pumped FIA systems in a CE-like configuration, the choice of the composition of the reaction system is limited because the composition must be such that EOF is generated at the desired level in the desired direction. Moreover, typically multiple line schemes are necessary in FIA, whereas a CE-like configuration is a single line scheme. Consequently, the CE-like configuration is inapplicable in many analytical applications, e.g., when the reaction must be carried out at very high or very low pH, in highly conductive saline solutions, or in a nonconducting organic medium. In all of these cases, electrical current levels are either excessive or inadequate to support significant EOF. Further, EOF has a flat profile, and the dispersion and dilution associated with a parabolic flow profile is desired, even necessary, in some FIA applications such as on-line dilution, gradient dilution techniques using a single standard, and FIA titration.

The art of FIA analysis would be improved by a reliable fluid propulsion device capable of handling low flow rates such that an overall miniaturization of the FIA system may be achieved; this device would preferably permit multiple line schemes, and would not significantly limit choice in composition of the reaction system.

SUMMARY OF THE INVENTION

The present invention utilizes EOF pumping and separates the EOF pumping system from the FIA chemical reaction system while maintaining hydraulic connectivity between them. The invention permits downscaling of a variety of FIA systems to flow regimes ranging from nanoliters per minute to microliters per minute without significantly limiting choice in the composition of the reaction system. The invention also permits FIA using multiple line schemes, and permits elimination of any electric field in the FIA reaction zone, which simplifies system considerations. Because of its rapid response to the applied high voltage and its bidirectional capabilities, an EOF pump may also be useful in sequential injection analysis.

One embodiment of the present invention is an apparatus for flow injection analysis, comprising: an electroosmotic pump having a grounding joint; a means for introducing a sample into a carrier stream which is in fluid communication with the grounding joint by way of a conduit; a dispersion means in fluid communication with the means for introducing the sample into the carrier stream; and a detector which is in fluid communication with the mixing means.

Another embodiment of the present invention is a method for flow injection analysis comprising the steps of: adding a volume of a sample to a liquid carrier stream to form a sample zone in the carrier stream; flowing a liquid pumping stream by electroosmosis; and connecting the pumping stream with the carrier stream to propel the carrier stream.

As a modification to the present invention, electrostacked flow-injection may be used for trace analysis. With the introduction of a membrane joint between a carrier holding coil and a sample injection valve, electrostacking can be performed in any type of FIA system and should be applicable for the preconcentration of most ionic analytes.

BRIEF DESCRIPTION OF THE DRAWINGS

FIG. 1 shows a schematic diagram of single-line FIA system with EOF pumping.

FIG. 2 is a partial cross-sectional view of the membrane joint assembly shown in FIG. 1.

DETAILED DESCRIPTION OF THE INVENTION

Figure 3:
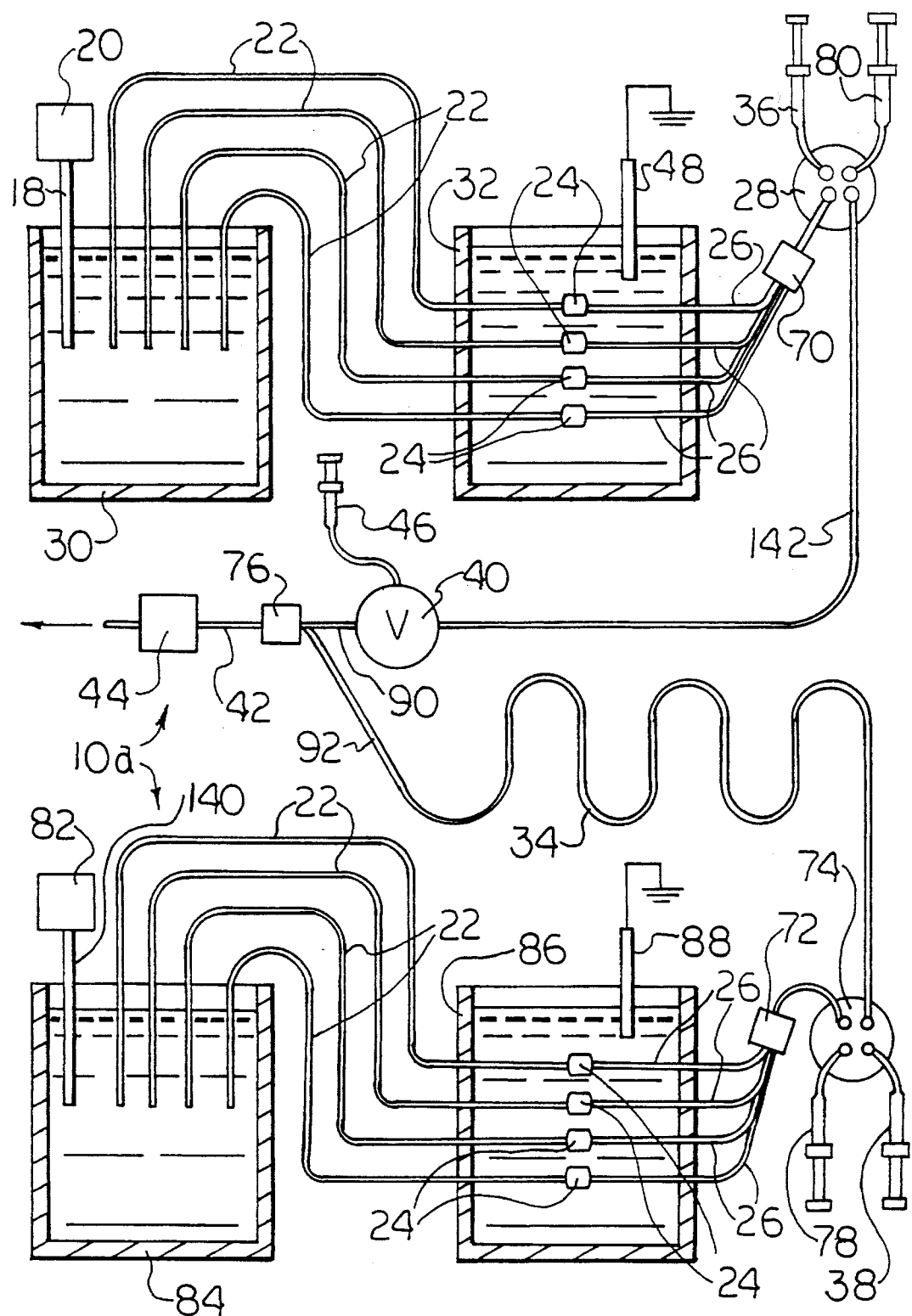
FIG. 3 is a schematic diagram of a double-line FIA system with EOF pumping.

Here and in the claims the term "electroosmotic pump" means a system having a conduit, such as a packed tube or a capillary, such that when a voltage is impressed along the conduit, a fluid in the conduit flows in the conduit by electroosmosis (EO). The flow of the liquid by EO can be used to propel a liquid of interest, such as a sample to be analyzed by FIA. Electroosmotic pumps are described in Liu and Dasgupta, *Anal. Chim. Acta,* 283 (1993) 739–745; and in U.S. Pat. No. 5,358,612 which are herein fully incorporated by reference. *Anal. Chim. Acta,* 283 (1993) 739–745 shows an example of electroosmotic pumping in flow injection analysis where no grounding joint is used. U.S. Pat. No. 5,358,612 shows a grounding joint using ion exchange tubing and discloses a combination of capillary electroosmosis and an electroosmotic pump.

The term "grounding joint" as used herein refers to a means of flowing electricity away from a fluid stream in a controllable position along the stream. An electrical ground can be established in an electroosmotic system without significant leakage of liquid by use of a porous glass or graphite joint, a porous frit, a crack in a capillary, or a conductive membrane. An example of an electrical ground in an electroosmotic system is described in U.S. Pat. No. 5,169,510 which is herein incorporated by reference. A palladium joint can also be used, but limits the system to a positive high-voltage polarity. (See, for example, Kok, W. Th. *Anal. Chem.* 1993, 65, 1853–1860.) Electrically conductive ion exchange membranes are convenient to use, for example, in a suppressed conductometric CE separation system. (See, for example, Dasgupta, P. K.; Bao, L. *Anal. Chem.* 1993, 65, 1003–1011.) In the present invention, such a membrane-based grounding joint is preferred.

A large volume of grounding electrolyte solution minimizes the change in composition of the electrolyte solution due to electrolysis which can affect EOF stability. Thus, the use of a larger container to hold the electrolyte solution helps stabilize the EOF.

The term "ion exchange membrane" as used herein refers to any ion exchange membrane as commonly known in the art. For example, U.S. Pat. No. 5,358,612, which has been incorporated by reference, describes various means for exchanging ions.

The term "means for introducing a sample" as used herein includes a sample injection valve which is, preferably, an inert electrically nonconducting valve of suitable low volume, a removable segment of conduit, and any other manual or automatic means for introducing sample as is commonly known in the art of FIA.

The term "dispersion means" as used herein refers to any means capable of providing mixing of a sample with a carrier stream which carries the sample to a detector, as is well known in the art of FIA. Preferably, the dispersion means is a length of tubing or a mixing chamber as is well known in the art if FIA.

The term "holding coil" as used herein means a conduit having a relatively large volume such that liquid flowed through the holding coil is retained for a sufficient period of time to provide adequate analysis. For example, a holding coil could be a packed column or a relatively long section of capillary tubing.

The term "pumping capillary" as used herein means a conduit capable of carrying a solution which is being pumped by electroosmosis. Better reproducibilities are believed to be obtained with fused silica capillaries as the pumping capillary; thus, silica capillaries, singly or in parallel, are preferred. However, it should be noted that an EOF pump need not be based on a silica capillary. Significant EOF can be generated conveniently using conduits of other material, such as many plastics and glasses, surface modified plastics and glasses, or columns filled with silica, clay, sponge, ion exchange resins, etc. Through appropriate choice of the operating voltage, electrolyte composition, and the number and dimension of the capillaries used, the invention can easily permit flow rates ranging from about one nanoliter per minute to about 100 microliters per minute, a span of 5 orders of magnitude.

As mentioned, the use of a silica capillary as a pumping element is preferred. The magnitude of the EOF generated is dependent on the extent of the surface charge of the capillary, as indicated by the zeta potential of the surface. For any given electrolyte, the zeta potential reaches its highest magnitude at low ionic strengths and, thus, the maximum EOF is observed at very low ionic strengths. For a silica surface, the EOF is also pH dependent, the ionization of surface-SiOH groups continues to high pH values. Consequently, as is well known, the EOF increases with pH up to a pH of about 9.

A borax electrolyte is a preferred pumping liquid for use in the pumping stream because borax is a nontoxic compound available inexpensively in a pure form, and the pH of a 2 mM borax solution (about 9.2) is in the range to produce optimum EOF. While even lower concentrations of the same electrolyte produce greater EOF, such solutions are too susceptible to contamination (including the absorption of atmospheric $CO_2$) and result in poor reproducibility. The term "pumping stream" as used herein means a stream of a liquid to be flowed directly by electroosmosis due to the application of an electric field along the pumping stream and its conduit.

The term "liquid carrier stream" as used herein means a stream of a liquid which is capable of carrying a sample of interest and which has essentially no electrical current passing through the stream due to the voltage applied to the pumping stream during operation. Thus, the current flowing through the liquid pumping stream, which causes it to flow by electroosmosis, is essentially isolated from the liquid carrier stream despite the hydraulic connection between the two streams.

The term "sample zone" as used herein refers to the region within the carrier stream in which sample is present immediately after the sample is introduced into the carrier stream.

The instant invention is the subject of a paper authored by Dasgupta and Liu in *Analytical Chemistry,* 1994, 66, 1792–1798, herein fully incorporated by reference.

Referring now to FIG. 1, therein is shown a single-line system 10 according to the present invention. An electroosmotic pump is arranged as follows. Pumping capillary 22 is connected via membrane grounding joint 24 to capillary 26 which is in fluid communication with one port of four-port valve 28. Membrane grounding joint 24, which is connected to one end of pumping capillary 22, is positioned within container 32 such that the membrane is covered by a grounding electrolyte solution within container 32. The opposite end of pumping capillary 22 is positioned within an electrolyte solution in container 30. High voltage supply 20 is electrically connected to electrode 18 which is positioned within the electrolyte solution in container 30. Another electrode 48 is grounded and positioned within the electrolyte solution in container 32. Membrane grounding joint 24, acts as a grounding joint for the electroosmotic pump described.

The other ports of valve 28 are in fluid communication with syringe 36 which holds pump buffer solution, syringe 38 which holds FIA reagent solution and holding coil 34. When valve 28 is in a first or operating position, capillary 26 is in fluid communication with a holding coil 34 through a port of valve 28. When valve 28 is in a second or flush and fill position, syringe 36 is in fluid communication with capillary 26 and syringe 38 is in fluid communication with holding coil 34. Holding coil 34 is in turn in communication with a sample injection valve 40. The sample injection valve acts as a means for introducing a sample into a carrier stream, and is in fluid communication with syringe 46, which holds sample, and with optical detector 44. The communication between the sample injection valve and optical detector 44 is via conduit 42 which serves as a dispersion means and typically is a mixing/reaction capillary. The optical detector 44 is in turn in fluid communication with a waste reservoir, not shown.

Referring now to FIG. 2, therein is shown a more detailed diagram of membrane grounding joint 24 of FIG. 1. Membrane grounding joint 24 comprises a tubular membrane segment 64 in which one end is held in communication with an end of capillary 22 by a segment of polyvinyl chloride (PVC) tubing 60 which has an end of pumping capillary 22 inserted therein. Similarly, the other end of tubular membrane segment 64 is held in communication with an end of capillary 26 by a segment of PVC tubing 62 which has an end of capillary 26 inserted therein. The tubular membrane segment 64 is held within the fluid in container 32 by securing pumping capillary 22 and capillary 26 to container 32 by a sealant 66, such as epoxy adhesive. The membrane segment 64 is preferably NAFION 014 brand ion exchange tubing from Perma Pure Products, Toms River, N.J.

Referring now to FIG. 3, therein is shown a double line system 10a according to the present invention which has two channels in communication with detector 44. Each of the two pumped channels has four pump capillaries 22 in parallel where each capillary is identical to the single pumping capillary 22 in FIG. 1 in its relationship to membrane grounding joint 24, and outlet capillary 26. In the first channel, the relationship of capillary 22 is the same as in FIG. 1 with respect to electrodes 18 and 48, high voltage supply 20, and containers 30 and 32. In the second channel, the arrangement of pump parts is the same as in channel one where electrodes 18 and 48, high voltage supply 20, and containers 30 and 32, correspond to electrodes 140 and 88, high voltage supply 82, and containers 84 and 86, respectively. Each pumping capillary 22 terminates in its own membrane grounding joint 24, the outlet capillaries 26 of the first channel were joined in common by union 70 and the outlet capillaries 26 of the second channel were joined in common by union 72. Unions 70 and 72 are connected to four-way valves 28 and 74, respectively. Four-way valve 28 is also in fluid communication with syringe 36 which holds pump buffer solution, and syringe 80 which holds carrier solution and carrier capillary 142. Carrier capillary 142 is connected to sample injection valve 40 which in turn is connected to tee 76 by a capillary 90. Sample injection valve 40 is in communication with syringe 46 which holds sample to be analyzed.

In addition to outlet capillaries 26 in the second channel, four-port valve 74 is also in fluid communication with syringe 78 which holds pump buffer solution, syringe 38 which holds reagent solution, and holding coil 34. Holding coil 34 is in fluid communication with reagent capillary 92 which is in turn in fluid communication with small volume tee 76. Small volume tee 76 is in fluid communication with detector 44 via conduit 42. From detector 44 liquid can flow to a waste reservoir, not shown.

Figure 4A:
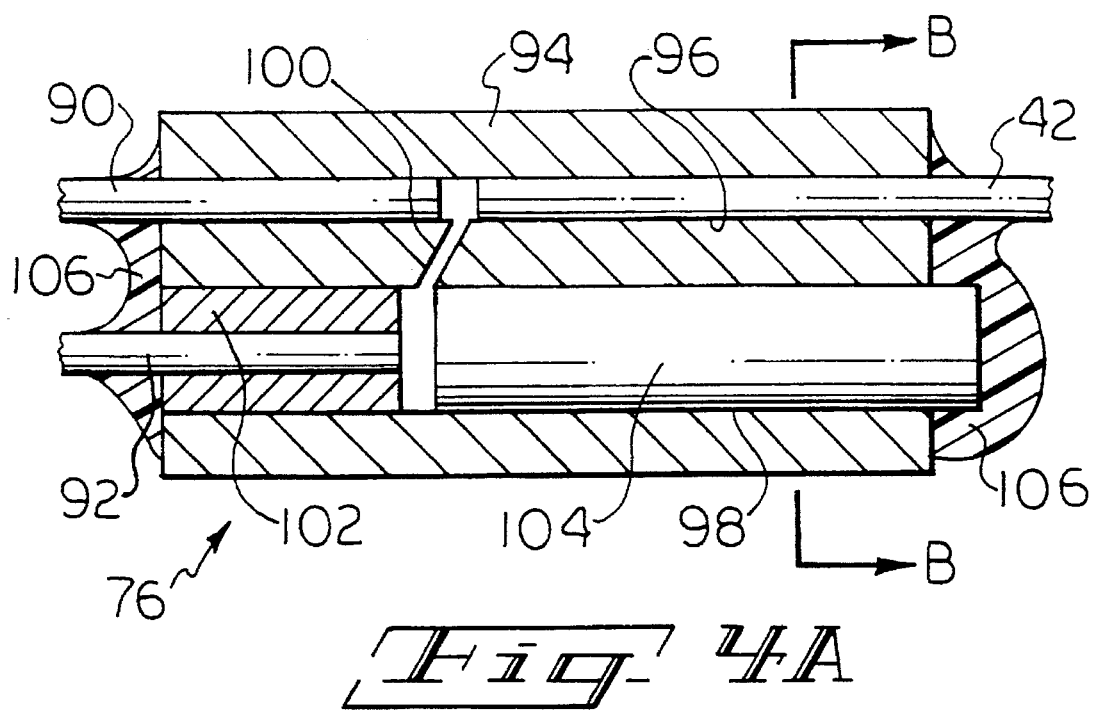
FIG. 4(a) is an axial cross-sectional view of the small volume tee of FIG. 3.
Figure 4B:
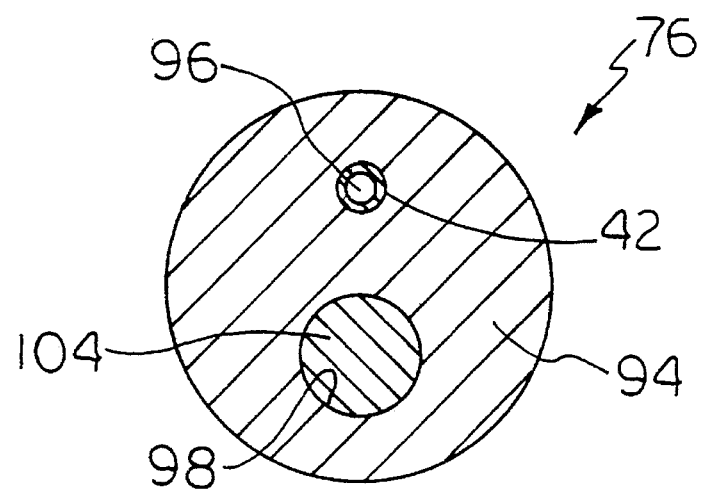
FIG. 4(b) shows a radial cross-sectional view of the small volume tee of FIG. 3.

Referring now to FIG. 4(a), therein is shown a more detailed diagram of the small volume tee 76 which is shown in FIG. 3. Tee 76 is a length of rod 94 having two separate parallel channels 96 and 98 therein in fluid communication with each other through a narrow channel 100. One end of channel 96 is connected to carrier capillary 90 by a sealant 106, such has an epoxy sealant; the other end of channel 96 is connected with capillary 42 by epoxy sealant 106. One end of the second channel 98 is connected to reagent capillary 92 with a sealant 106, such has an epoxy sealant, and with a piece of PVC tubing 102 as a space filler; the other end of channel 98 is blocked off with a blocking rod 104. FIG. 4(b) shows a crosssectional view of the rod 94 along view B—B of FIG. 4(a).

The method of the present invention may be employed as follows. Generally, the method utilizes one fluid which is electroosmotically pumped to propel another fluid for flow injection analysis at a controllable flow rate. More specifically, the method comprises the steps of: adding a sample to a liquid carrier stream to form a sample zone in the carrier stream; flowing a liquid pumping stream by electroosmosis; and connecting the pumping stream with the carrier stream to propel the carrier stream.

The method of the present invention may be described by reference to the apparatus depicted in FIG. 1, a sample from syringe 46 is injected into a carrier stream located within holding coil 34 and reaction capillary 42 via sample injection valve 40. When sample injection valve 40 is positioned such that fluid communication is provided between holding coil 34 and reaction capillary 42, the sample in sample injection valve 40 forms a sample zone in the carrier stream which is carried along in the stream towards the detector 44. The carrier stream is propelled by a liquid pumping stream which is located in pumping capillary 22. The liquid pumping stream flows by electroosmosis when a voltage is applied along pumping capillary 22. Appropriately positioning valve 28 provides fluid communication between holding coil 34 and capillary 26.

More importantly, membrane grounding joint 24 provides hydraulic communication between the pumping stream in capillary 22 and the carrier stream, while simultaneously electrically isolating the two streams by acting as a grounding joint. The connection between the two streams, which is provided by membrane grounding joint 24 and valve 28, permits the pumping stream to propel the carrier stream when the pumping stream flows by electroosmosis. Because the pumping stream and the carrier stream are electrically isolated, the method of the invention may be used, for example, to propel carrier fluids that are essentially electrically too conductive or too resistive to be pumped directly by electroosmosis. Electrically unconductive means having a conductance of less than about one microsiemens per centimeter. Being electrically too conductive to be directly pumped by electroosmosis means having a conductance of more than about 100 millisiemens per centimeter. When the pumping and the reaction systems are separated, the carrier/reagent need not pass through the electroosmotic pump. In fact, strongly acidic, alkaline, or saline reagents can be difficult to pump by direct electroosmosis.

The EOF generated by the method of the invention is dependent on the applied voltage and/or the current flowing through the capillary. The flow rate exhibits a generally linear relationship with the current. As further evidence of a direct relationship of the flow rate with current, the following observations can be cited: (a) if the outlet hydrostatic resistance to an EOF pump is increased, the resulting drop in flow rate is accompanied by a decrease in current at the same applied voltage (albeit the current does not drop to zero at zero flow rate); (b) within a limited range of capillary diameter, e.g., 75–150 μm, the EOF has relatively little dependence on the capillary diameter, as long as the current flowing through the capillary is held constant. In contrast, at constant voltage, the current and the generated EOF through a larger capillary is substantially greater.

If the pump electrolyte is appropriately chosen, at typical capillary dimensions, the electrical current level demanded of the power supply is substantially less than its maximum capability, even at maximum applied voltage. Larger capillary diameters generate greater EOF at the same voltage, however, the greater flow rate capability of a larger capillary is more than offset by the fact that the flow from larger capillaries is much more susceptible to flow rate decreases due to backpressure.

The susceptibility of the EOF pump rate to backpressure must be taken into consideration in designing the components downstream of the EOF pump. A conduit of diameter D and length L represents the same dwell time as a conduit of diameter 2D and length L/4. However, at any given pumping rate, the backpressure represented by the second reaction conduit is 1/64th that of the first. Limitations of an EOF pump regarding pumping against backpressure can be largely overcome by appropriate selection of conduit diameters. For this reason, reaction conduits of significantly greater diameter than those of the pump capillaries (typically 250 μm bore holding coils and 150 μm bore conduits with 75 μm bore pumps) are used so minor changes in backpressure, such as those caused by thermally induced changes of viscosity, will be negligible.

After a period of time, the holding coil may become contaminated by the pump fluid. The operating period can be extended by increasing the volume of the holding coil to delay contamination. The most efficient use of the volume in the holding coil is made if an immiscible fluid plug or a small segment of air can be introduced between the pump fluid and the reagent.

Introduction of air bubbles into the pumping capillary could potentially result in pump malfunction via circuit disconnection. However, if the pumping electrolyte is carefully chosen and degassed, if desired, such problems are unlikely.

Referring now to FIG. 3, the electroosmotic pumps in channels one and two may be used the same way as described above for the apparatus of FIG. 1, with the exception that voltage is applied across more than one pumping capillary 22 in each channel to increase the total flow rate in each channel. A holding coil is not necessary in the first channel of FIG. 3 because the pumping stream and the carrier stream are of the same composition.

As shown in FIG. 3, a single high voltage power supply can support a multiplicity of pumping channels. Such multi-line pumping can improve sample throughput. The magnitude and the direction of the flow are easily adjusted by respectively changing the magnitude or the polarity of the applied potential. The pumping system has intrinsic high reliability because there are no moving parts. If there is any perceptible change in flow rate over time (readily apparent from the interval between injection and detection), the flow rate can be maintained constant by direct feedback control of the programmable power supply. When more than one pumping channel is to be used, different flow rates can be achieved by changing the type or dimensions of the pumping element or, more practically, by controlling the current through variable resistors.

Turning now to another embodiment of the present invention, the ionic analytes in a sample can be concentrated via electrostacking by applying an electric field across the carrier-sample-carrier segment. Electrostacking may be done because the carrier solution can be made considerably more conductive than the sample solution by the addition of an inert electrolyte. Thus, the method of the present invention may be employed with the further step of electrostacking the sample zone by applying a voltage across the sample zone wherein the voltage applied across the sample zone is electrically isolated from the voltage applied to the liquid pumping stream. When a large volume of sample is introduced, the concentrated analyte zone becomes wide. Optical detection sensitivity can be further improved in this case by using a larger bore detection capillary.

Figure 5:
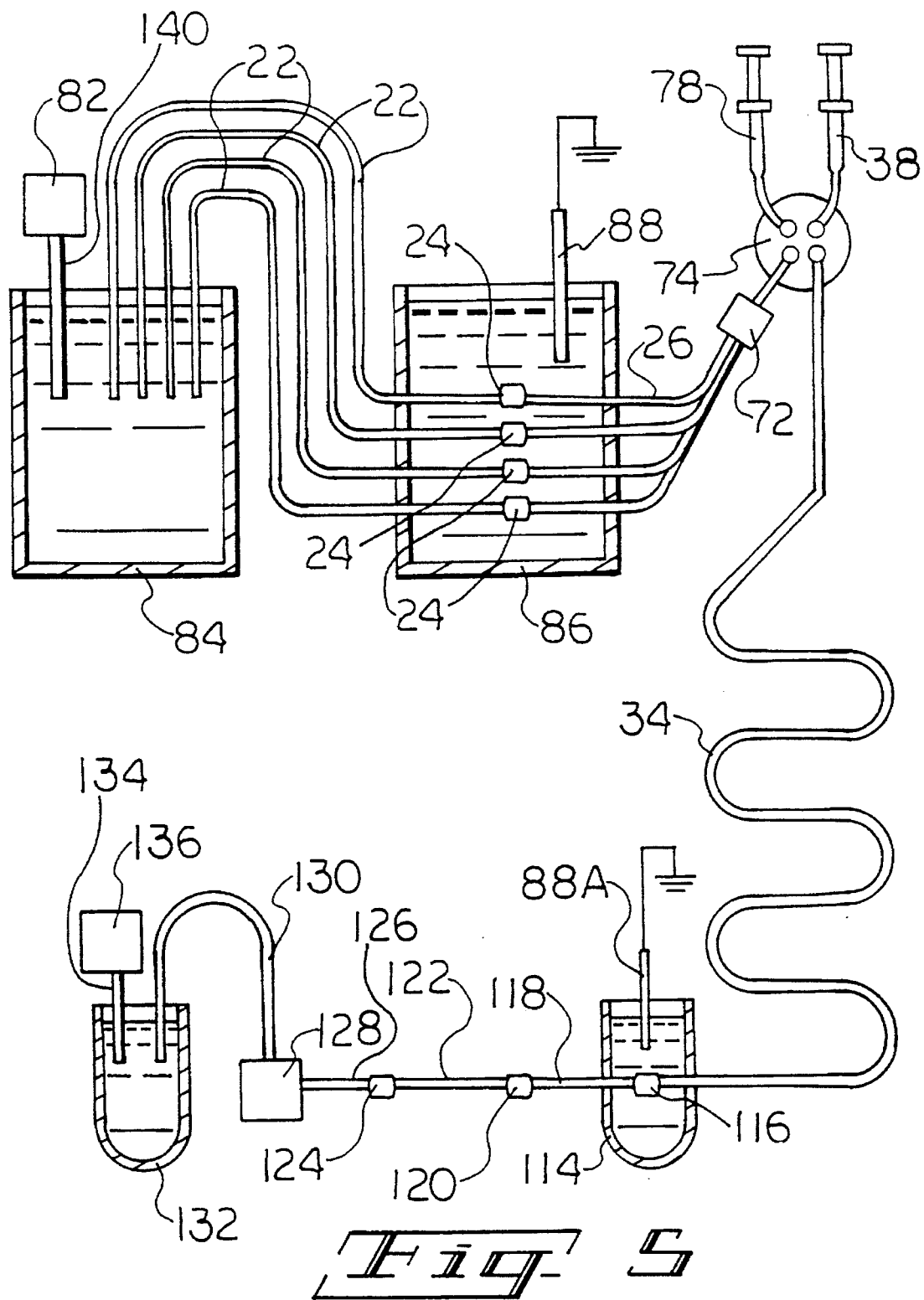
FIG. 5 is a schematic diagram of an arrangement for electrostacking concentration in FIA while using an EOF pump.

Referring now to FIG. 5, therein is shown an apparatus which has an electroosmotic pump similar to that depicted in the second channel of FIG. 3 from high voltage supply 82 to holding coil 34. The apparatus of FIG. 3 can be adapted to provide electrostacking by the following changes to the apparatus. Holding coil 34 is in fluid communication with membrane grounding joint 116 which is positioned within the electrolyte solution in container 114 together with grounded electrode 88a. Membrane grounding joint 116 is in fluid communication with capillary 118 which is in communication with a means for introducing sample, which will be described below. Reaction capillary 126 connects detector 128 with the sample introducing means. Detector 128 is in turn in fluid communication with the electrolyte solution in container 132 via capillary 130. High voltage power supply 136 is in electrical communication with the liquid in container 132 via electrode 134. High voltage power supply 136 may be used for preconcentration of the sample by the electrostacking method.

In addition to the changes to provide electrostacking, the sample injection valve 40 of FIG. 3 was replaced with a capillary 122 to demonstrate manual sample introduction while using the present method. Capillary 122 is a detachable capillary segment which can be taken off-line, filled with sample, and replaced on-line in fluid communication with reaction capillary 126 and capillary 118 by connection to PVC tube segments 124 and 120, respectively.

The method employing electrostacking may be executed in different modes after the sample is introduced. Referring to FIG. 5, what shall be referred to as mode 1, consists of applying voltage using high voltage power supply 136 for a period of time to provide electrostacking concentration, turning off high voltage power supply 136, and then turning on high voltage power supply 82. Mode 2 involved applying high voltage from power supplies 82 and 136 simultaneously.

A comparative mode 3 represents a standard EOF pumped FIA system with such a large amount of injected sample that the dispersion factor is unity. In mode 3, no attempt is made to stack the analyte, so only high voltage power supply 82 is applied.

In modes 1 and 2, the high voltage power supply 136 is operated in the constant current mode. The voltage falls during the preconcentration process. The final voltage of power supply 136 can be made small enough to have little adverse effect on the whole system by choosing the maximum current limit at a suitably low value. Thus, the system can be continuously operated with on-line electrostacking concentrations.

Generally, mode 2 is preferred because it takes less time for each measurement. However, if the sample matrices vary considerably in ionic strength, peak area based calibration in this mode may be difficult. The flow rate will change as the voltage and the current on high voltage supply 136 change with time. In such cases, mode 1 may be a better choice for quantitative accuracy unless a method is developed to track flow rate continuously.

EXAMPLE 1

A single-line system for the determination of ferric iron is arranged as shown in FIG. 1. A programmable high-voltage power supply CZE1000PN30, ±30 kV max, is used (available from Spellman High Voltage, Plainview, N.Y.). A polyimide coated fused silica pumping capillary 22 of 40 cm×75 μm i.d. ×375 μm o.d. (available from Polymicro Technologies in Phoenix, Ariz.) is connected by a membrane joint 24 to another capillary 26 (ca. 10 cm×250 μm i.d. ×355 μm o.d.) which terminates in a four-way valve 28.

One end of pumping capillary 22 is inserted into a pump electrolyte container 30 (2 mM $Na_2B_4O_7$). The membrane joint 24 is fixed inside a container 32 ranging in capacity from a 1.5-mL vial to a 25-mL plastic bottle. Container 32 contains the same solution as container 30 and is electrically grounded.

Details of the membrane joint 24 are shown in FIG. 2 as discussed above. The membrane joint is made from the NAFION 014 brand tube discussed above that is heated and stretched to reduce its diameter. Capillary termini of pumping capillary 22 and capillary 26 are inserted into an ethanol-swollen membrane segment 64. After allowing the solvent to evaporate, segments of PVC tubing (5 mm×200 μm i.d. ×2 mm o.d., Elkay Products, Inc., Shrewsbury, Mass.) are forcibly inserted on each side of the membrane joint to prevent liquid leakage when the joint is immersed in solution during operation and the membrane swells.

Valve 28 is a double stack four-port valve (Dionex Inert Valve, Dionex Co., Sunnyvale, Calif.). Only one stack is necessary for a single pumped channel. During operation the valve ports are connected, as shown, such that pumping capillary 22 is in fluid communication with regent holding coil 34 (3 m×250 μm i.d. ×350 μm o.d.; 150 μL volume). Prior to or after operation, the valve ports of four-way valve 28 are positioned such that a syringe 36 holding pumping electrolyte (pump buffer solution) and a syringe 38 holding reagent solution flush and fill the pumping capillary and holding coil, respectively. The pump electrolyte buffer solution for all experiments described herein is 2 mM $Na_2B_4O_7$. The reagent for $Fe^{3+}$ determination is 10 mM xylenol orange (XO, Aldrich) in 50 mM $HNO_3$.

The sample injection valve (Valco Instruments, Houston, Tex.) is an electrically actuated dual internal loop valve with wetted parts of Kel-F/Teflon. A sample injection volume of a 60 nL sample of $Fe(NO_3)_3$ in 10 mM $HNO_3$ is used. The load/injection periods for the sample injection valve (60/360 s) are controlled by a programmable microcontroller (LS-100, Minarik Electric, Los Angeles, Calif.).

A conduit or mixing/reaction capillary 42 (15 cm×150 μm i.d. ×375 μm o.d.) served as a mixing and reaction coil. An optical detection window is made by removing the polyimide coating on mixing/reaction capillary 42 for about 1 cm at a distance of about 4 cm from sample injection valve 40.

Optical detector 44 (206 PHD, Linear Instruments/Spectra Physics) is equipped with an I/O interface for personal computer based data acquisition. From the detector 44 liquid flows to a waste reservoir.

A voltage of 15 kV is applied across the pumping capillary 22 by applying a voltage between electrode 18 and electrode 48 in containers 30 and 32, respectively, to cause the pumping solution to flow by electroosmosis. When valve 28 and sample injection valve 40 are in a position to permit fluid communication between the pumping capillary 22 and the detector 44, the electroosmotic flow in pumping capillary 22 causes the liquid in the holding coil, and, hence, the sample along with the carrier solution, to be pumped into the detector 44. Flow rates may be measured gravimetrically or by measuring the rate of movement of a liquid meniscus in a capillary of known inner diameter.

The output flow rate obtained from the pump is about 500 $nL/min^{-1}$ with 15 kV applied. The flow rate remained essentially the same when the holding coil and the downstream components are linked to the pump. For the $Fe^{3+}$ determination system, the peak height reproducibility is excellent, with a relative standard deviation (RSD) of 0.82% (n=12). The sample throughput is about nine samples per hour. Although the reagent-holding capillary had a capacity of only 150 μL, the system runs for at least 180 minutes without refilling. Alternatively, when two pumping capillaries 22 are used and a 25 mL plastic bottle 32 is used to hold the solution grounding the membrane grounding joints, the system can be run for about 165 min without refilling, with sample injection every 3 minutes with a peak height relative standard deviation of about 0.4%.

EXAMPLE 2

An arrangement of a two-line system for the determination of chloride is shown in FIG. 3. Each of the two pumped channels uses four capillaries in parallel (each identical to the single pump capillary in FIG. 1). Each pump capillary terminates in its own membrane grounding joint, the outlet capillaries of channel one are joined in common by union 70, and the outlet capillaries of channel two were joined in common by union 72 before being connected to four-port valves 28 and 74, respectively. Unions 70 and 72 are constructed from PVC tubes and silicon sealant. Since the pump electrolyte itself is used as the carrier in which the sample was injected by sample injection valve 40 (100 nL injection volume, load/injection cycle 60/120 s), a holding coil is not necessary in the first channel. A holding coil 34 is used in the reagent pumping second channel. Syringes 36 and 78 are filled with the pump electrolyte solution, while syringes 80 and 38 contain the carrier and the reagent solution. After the system is flushed and filled with the appropriate solutions in the same manner as described with respect to FIG. 1, four-way valve 28 is switched to the working position shown in FIG. 3.

With the exception of union 76, the equipment used for the apparatus of FIG. 3 can be the same type as described in example 1. Union 76 which provides fluid communication between capillaries 90 and 92, preferably has a small hold up volume to minimize undesired dispersion. Union 76 is made from a double bore PTFE tubing product (Zeus Industrial Products, Raritan, N.J.), one bore with about 350 μi.d. and the other bore with about 1.9 mm i.d. To make a connection between the two bores, an oblique hole 100 is drilled between them as shown in FIG. 4. Multiple bore tubing, with all conduits of very small diameter, is also available. However, when one of the conduits has a relatively large bore, it is possible to drill the interconduit connection through the end face of the tube. This way, the outer wall need not be punctured. The carrier stream capillary 90 from the injection valve 40 and the detection capillary 42 are inserted into opposite sides of the smaller conduit 96 with a gap of about 1 mm between them at the aperture from the other channel. The reagent capillary 42, with a segment of PVC tubing 102 atop the terminus as a space-filling element, is inserted into one end of the larger conduit 98. The other end of the large conduit 98 is blocked with a PTFE rod 104 and covered by epoxy sealant 106. Mixing/reaction capillary 42 is the same as in FIG. 1. The detection window was located about 4 cm from tee 76.

The procedures of preparing reagent and sample stock solutions for chloride are taken from the standard method for chloride measurement as is known in the art. The chromogenic reagent for chloride is composed of three parts of a mercuric thiocyanate stock solution (13 mM $Hg(SCN)_2$ in methanol) and two parts of a ferric nitrate stock solution (0.5M $Fe(NO_3)_3 \cdot 9H_2O$ in 0.3M $HNO_3$). The carrier stream is the same as the pump electrolyte. The chloride sample solutions are made by appropriate dilution of a 1000 ppm stock solution.

For the two-channel system for chloride determination, the use of four pumping capillaries in parallel resulted in a flow rate of 1.7 $\mu L \cdot min^{-1}$. The sample throughput for 1% carryover increases to 40 samples per hour. Peak height reproducibility at each concentration level is less than about 0.8% (n=13).

EXAMPLE 3

The experimental setup for electrostacking is shown in FIG. 5. The membrane grounding joint 116 connects the carrier electrolyte holding coil 34 and the sample injection valve. The sample injection valve is composed of a detachable capillary segment 122 (10 cm×150 µm i.d. ×375 µm o.d. with a volume of about 1.8 µL). Each end of capillary segment 122 is connected with PVC tube segments 120 and 124 to upstream and downstream conduits. In these experiments, the sample is manually introduced by taking capillary 122 off-line, filling it with sample, and putting it back in the system. This arrangement can be replaced with an inert electrically nonconducting valve of suitably low volume. High voltage supply 82 is a second high-voltage power supply used for preconcentration. Other components are similar to those in FIG. 3. Bromocresol green (BCG, MC & B) 10 µM in concentration and containing 10 µM $Na_2B_4O_7$ is used as the sample and 0.1M $Na_2B_4O_7$ is used as the carrier for the electrostacking/flow-injection experiments of example 3.

This apparatus is used as described for modes one through three in the description of the invention above. Operating in mode 1, the voltage from high voltage supply 136 is applied for two minutes. The sample is concentrated by more than 5-fold using modes 1 and 2 relative to mode 3. With optimized experimental parameters, a greater degree of preconcentration should be achieved.

In modes 1 and 3, the flow rate through the detector is the same. The flow rate in mode 2 is higher with both high voltage supplies 82 and 136 applied. The reproducibilities in these experiments are limited by the nature of the manual sample introduction technique.

The bromocresol green (BCG) migration time in mode 1 is longer than that in mode 2 because of a preconcentration time of 2 min used with mode 1. In these experiments, high voltage power supply 136 is operated at 10 kV with a preset maximum current of 100 µA. When high voltage power supply 136 is being applied in modes 1 and 2, the voltage is constant at 10 kV only initially. As the conductance of the solution between containers 114, and 132 became high due to dispersion and the diffusion of the carrier electrolyte into the initially poorly conductive sample zone, the voltage falls after the current limit of 100 µA is reached. The voltage decreases until a final stable voltage of about 2 kV is reached when all of the sample zone is carried out of the detection capillary 130.

For interpretation of results obtained, under the particular conditions described, the peak heights obtained applying modes 1 and 2 appear the same. However, this is not true under all conditions. For instance, if the length of the mixing/reaction capillary 126 is increased, peak heights are reduced in both modes, but mode 1 is affected more.

What is claimed is:

1. A flow injection analysis apparatus, comprising:
   (a) an electroosmotic pump having a grounding joint;
   (b) a means for introducing a sample into a carrier stream, the means for introducing a sample into a carrier stream being in fluid communication with the grounding joint by way of a conduit;
   (c) a dispersion means in fluid communication with the means for introducing the sample into the carrier stream; and
   (d) a detector, the detector being in fluid communication with the dispersion means wherein the means for introducing a sample is positioned between the grounding joint and the detector.

2. The apparatus of claim 1 wherein the conduit is a holding coil so that a first liquid can be flowed within the electroosmotic pump and a second liquid can be positioned in the conduit.

3. The apparatus of claim 1 wherein the grounding joint comprises an ion exchange membrane.

\* \* \* \* \*